United States Patent [19]

Lin et al.

[11] Patent Number: 5,075,503
[45] Date of Patent: Dec. 24, 1991

[54] HYDRAZINE TERMINATED POLYOXYALKYLENE AMINES

[75] Inventors: Jiang-Jen Lin, Houston; George P. Speranza, Austin, both of Tex.

[73] Assignee: Texaco Chemical Company, White Plains, N.Y.

[21] Appl. No.: 576,826

[22] Filed: Sep. 4, 1990

[51] Int. Cl.$^5$ ............................................ C07C 243/34
[52] U.S. Cl. ...................................... 564/151; 528/111
[58] Field of Search ......................... 564/151, 150, 159

[56] References Cited

U.S. PATENT DOCUMENTS 3,061,642 10/1962 Weisse et al. .......................... 564/151
3,450,673 6/1969 McKillip .............................. 564/151
4,530,991 7/1985 Hirai et al. ........................... 564/151

OTHER PUBLICATIONS

Hook et al., *Chemical Abstracts*, 112 (11): 91218x, (1990).

Primary Examiner—Glennon H. Hollrah
Assistant Examiner—Scott C. Rand
Attorney, Agent, or Firm—Jack H. Park; Kenneth R. Priem; Cynthia L. Kendrick

[57] ABSTRACT

Disclosed are novel hydrazine terminated polyoxyalkylene amines which contain active hydrazine, secondary amines, flexible ether groups and amide functionalities in the same molecule. They are prepared in a two-step reaction which can be represented by the following:

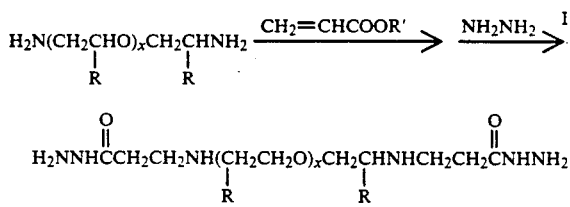

where R=H or $CH_3$ and $R^1$=$CH_3$ or $CH_2CH_3$. The products are used for epoxy curing agent and chain extender for polyurea polymers.

5 Claims, No Drawings

HYDRAZINE TERMINATED POLYOXYALKYLENE AMINES

FIELD OF THE INVENTION

This invention relates to the preparation of new hydrazine terminated polyoxyalkylene amines. In particular this invention relates to novel hydrazine terminated amines prepared in two steps from the reaction of a polyoxyalkylene amine, such as a JEFFAMINE® amine, acrylate and hydrazine. The products are liquid and the hydrazine and secondary amino groups contained within the same molecule can display different reactivities, thus making the products especially suitable as latent epoxy curing agents.

DESCRIPTION OF RELATED ART

Some hydrazine compounds are known in the art for their effectiveness when incorporated in curing agents. U.S. Pat. No. 4,544,733 discloses a one-pack type epoxy resin composition which effectively cures at low temperatures and provides for superior storage which comprises a hydrazide compound having one of the following general formulas:

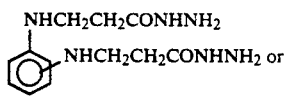

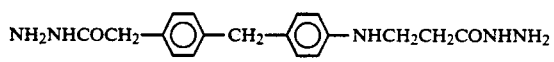

In U.S. Pat. No. 4,598,121 there is disclosed a method of reacting a diamino hydrazide with a prepolymer having free NCO groups, said prepolymer prepared by the reaction of an aliphatic or cycloaliphatic polyisocyanate with a polyol and an anionic compound and dispersing the prepolymer in water and reacting the product with formaldehyde to effect cross-linking.

U.S. Pat. No. 4,448,949 discloses a hydrazide compound of the formula:

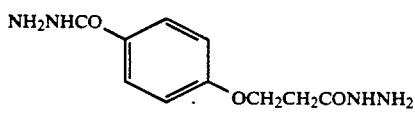

which alone or in combination with other curing agents can activate a rapid curing of epoxy resin compositions at relatively low temperatures and yet be extraordinarily resistant to gelling at 40° C. for substantial periods of time.

In U.S. Pat. No. 4,530,991 there is disclosed a composition comprising hydrazides of the formula:

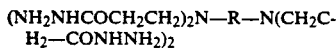

where R is a divalent hydrocarbon residue having 2–24 carbon atoms which are useful as latent curing agents.

There is a continuing need in the art for epoxy curing agents which have latent curing properties, are resistant to gelling or exhibit other desirable properties. Nowhere in the art described does it appear that a polyoxyalkylene amine has been incorporated into a hydrazine terminated molecule to use as a curing agent. The polyoxyalkylene group in the molecule will enhance the polymer product's flexibility and, depending which polyoxyalkylene amine is used, will make the composition tailored for specific applications.

In the instant invention it has been discovered that novel compositions can be prepared which contain hydrazines as well as secondary amine groups. The presence of the secondary amine groups allows for properties which would not be observed in the products of related work. The hydrazine terminated polyoxyalkylene amines are liquid which facilitates easier handling and the secondary amine and hydrazine groups have different reactivities which offer latent curing properties.

SUMMARY OF THE INVENTION

It is an object of the present invention to provide a method of preparing novel hydrazine terminated polyoxyalkylene amines which provides products having properties very suitable for a variety of applications as latent epoxy curing agents or as chain extenders for polyurea applications.

More specifically, in accordance with the present invention, there is provided a method for the preparation of hydrazine terminated polyoxyalkylene amines which comprises reacting a polyoxyalkylene amine, acrylate and hydrazine in two steps at a temperature of about 50° to 150° C. and atmospheric pressure.

The product compositions can be represented by the general structure:

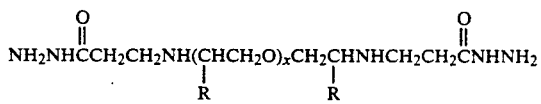

where x is a positive integer from 1 to 6 and R is H, $CH_3$ or $C_2H_5$.

The novel products prepared by the newly developed experimental procedures have the following advantages in various applications:

1) Flexibility: Provides extension of unique JEFFAMINE® amines which includes a family of different molecular weight polyoxyalkylene polyamines.
2) Multiple Functionalities: Includes amide and polyether functionalities in the same molecule.
3) Different Amine Activity: Containing active hydrazine and less active secondary amines, the combination of which is particularly suitable for the purpose of latent curing
4) Low Viscosity/Color: These are good properties for liquid products.

DETAILED DESCRIPTION OF THE INVENTION

The novel hydrazine terminated polyoxyalkylene amine represented by the general structure above can be synthesized in two steps by reacting a polyoxyalkylene amine with acrylate to form a polyoxyalkylene amine-acrylate adduct which is subsequently reacted with hydrazine.

The two step method can be represented by the following:

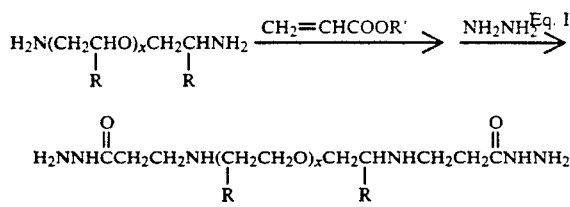

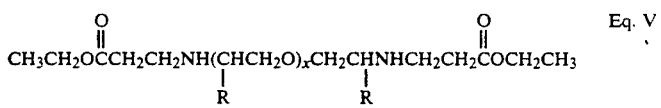

where R=H or CH₃ and R'=CH₃ or CH₂CH₃.

The polyoxyalkylene polyamine starting material may be broadly defined as a polyoxyalkylene polyamine having the formula:

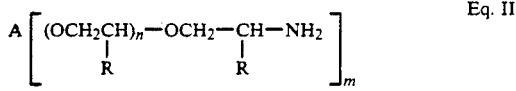

wherein A is the nucleus of an oxyalkylation-susceptible polyhydric alcohol containing 2 to 12 carbon atoms and 2 hydroxyl groups and R is hydrogen or methyl, n is a number having an average value of 0 to 3, and m is an integer having a value of 2.

Polyoxyalkylene polyamines which work well as demonstrated in Examples I-XII are polyoxyalkylene diamines. In general, the average molecular weight of the polyoxyalkylene diamine starting material will be from about 100 to about 400.

One group of suitable polyoxyalkylene amine reactants are polyoxyethylene diamines of the formula:

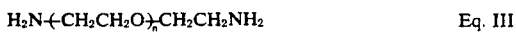

where n is 2 or 3.

Representative products having this structural formula include "JEFFAMINE ® EDR series diamines". JEFFAMINE ® EDR-148 is the trademark for triethylene glycol diamine produced by Texaco Chemical Co. and JEFFAMINE ® EDR-192 is the trademark for tetraethylene glycol diamine, also produced by Texaco Chemical Co.

Another group of appropriate polyoxyalkylene diamines that may be used are those sold by the Texaco Chemical Co. as JEFFAMINE ® D-series products having the formula:

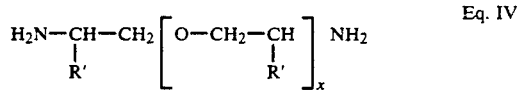

wherein R' independently represents hydrogen or methyl and x is a number having an average value of about 1 to about 6.

Representative products having this structural formula include a polyoxypropylene diamine having an average molecular weight of about 230 wherein x has a value of 2-3 (JEFFAMINE ® D-230) and a polyoxypropylene diamine having an average molecular weight of 400 wherein x has a value between about 5 and 6 (JEFFAMINE ® D-400 amine).

The polyoxyalkylene amine is reacted with an acrylate. Suitable acrylates are those represented by the formula CH₂=CHCOOR where R is an alkyl group having 1 to 8 carbons. Representative acrylates include butyl acrylate, propyl acrylate, methyl acrylate and ethyl acrylate. The examples demonstrate the effectiveness of ethyl acrylate.

The addition of the acrylate to the polyoxyalkylene amine is a slightly exothermic reaction. The resulting polyoxyalkylene amine-acrylate adduct can be represented by the following structure:

$$CH_3CH_2OCCH_2CH_2NH(CHCH_2O)_xCH_2CHNHCH_2CH_2COCH_2CH_3 \quad \text{Eq. V}$$

where R is H, methyl or ethyl and x is 1 to 5.

The above-described amine-acrylate adduct is further reacted with hydrazine (NH₂NH₂) which is commercially available and can be handled easily.

It has been discovered in accordance with the present invention that a new product containing hydrazine-amine, polyoxyalkylene and secondary amine functionalities is formed when a polyoxyalkylene amine is reacted with an excess of an acrylate and subsequently, with an excess of hydrazine. The product can be liquid to semisolid or solid and light or clear in color.

The reaction in the first step is slightly exothermic, however additional heating is necessary after the initial reaction. The mixture will require heating to a temperature of from about 50° C. to 150° C. Preferably the temperature in the first step is from 60° C. to 80° C. It is helpful if the amine-acrylate adduct is heated at fairly mild temperatures for a period of from about 1 to 10 hours.

In the second step, after addition of the hydrazine, the mixture is heated to a temperature of from about 50° C. to 150° C. Ideally the mixture is heated slowly to a temperature of from 70° to 140° C. over a period of about 3-6 hours.

A solvent is useful in the second step for the introduction of hydrazine to the reactor. Where a solvent is used it is preferably a polar solvent. Solvents which will work include water and oxygenated hydrocarbons, particularly those where the only oxygen atoms present are in the hydroxyl groups of alcohols such as methanol and ethanol.

With regard to the molar ratios, it is generally desirable to have a slight excess of acrylate to amine. In the first step a molar ratio of amine groups to acrylate of about 1:2 was generally acceptable. Good results were obtained in the first step using a molar ratio of about 0.9 to 1 moles of amine to about two of acrylate.

Likewise, in the second step a slight excess of hydrazine is preferred. Molar ratios of 1:2 to 1:5 of amine-acrylate adduct to hydrazine can be used. Molar ratios of 1 mole of amine-acrylate adduct to 2 to 5 moles of hydrazine can be used and preferably about 2 to 2.1 moles of hydrazine per mole of amine-acrylate adduct. The excess of hydrazine is used to ensure good product properties or avoid the polymerization.

The novel compositions that are formed by the process of the invention are colorless or light colored viscous liquids or semisolids having a molecular weight within the range of 270 to about 2500 and preferably within the range of 270 to about 650. They exhibit a hydrazine-amide functionality as well as a unique polyoxyalkylene amine and secondary amine functionality. Within the same molecule the hydrazine and secondary amine groups behave differently in terms of their reactivities. Therefore they are especially useful in applications as latent epoxy curing agents. They are also useful as chain-extenders for polyurea applications.

Where the novel compositions are used as curing agents to make coatings it is possible to produce a very hard, nearly colorless polymer.

Products have been identified in this work by amine titration, $C^{13}$ nmr or H-NMR.

The following examples illustrate the novel process of this invention. The examples are only for the purpose of illustration and are not intended to limit the invention in any way.

EXAMPLE I

The preparation of hydrazine-terminated JEFFAMINE ® amines required a two-step reaction:

(A) Preparation of JEFFAMINE ® amine-acrylate adduct.

To a 500 ml 3-necked flask equipped with a thermometer, a Dean-Stark trap, a mechanical stirrer and nitrogen inlet line was charged ethyl acrylate (200 g, 2.0M). Then EDR-148 (148 g, 1.0M) was added slowly. The exothermic temperature at 39° C. was recorded. The mixture was heated to 60°–65° C. for ca. 8 hours. The recovery product was a colorless liquid. The H-NMR indicated the structure (A). The amine content was 5.8 meq/g (calc. 5.7 meq/g).

EXAMPLE III

Hydrazine-terminated JEFFAMINE ® EDR-148
(Prepared at lower temperature)

To a 500 ml 3-necked flask equipped with a thermometer, a Dean-Stark trap, a stirrer and nitrogen-line, was added ethyl acrylate (100 g, 1.0M). Then JEFFAMINE ® EDR-148 (74 g, 0.5M) was added. The exothermic temperature was 70° C. The mixture was heated and the temperature maintained at 60° C. for 5 hours. After cooling to room temperature, hydrazine (32 g, 1.0M) in methanol (30 ml) was added. The reaction temperature was maintained at 85°–90° C. for ca. 4 hours. The product obtained was very light colored viscous liquid. The analysis indicated 11.9 meq/g total amine (calc. 12.3 meq/g) and viscosity 9200 cs/25° C.

EXAMPLE IV

Hydrazine-terminated JEFFAMINE ® EDR 192
(Prepared at lower temperature)

The above experimental procedures were repeated except using EDR-192 instead of EDR-148. The final product was a light colored liquid with analyses of 10.2 meq/g for total amine (calc. 10.9 meq/g) and viscosity at 7200 cs/25° C.

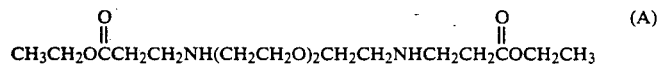

(A)

(B) Reaction product from hydrazine and JEFFAMINE ® amine-acrylate adduct.

To a 250-ml 3-necked flask equipped with a thermometer, a Dean-Stark trap, a stirrer and nitrogen inlet line was charged JEFFAMINE ® EDR-148-acrylate adduct (90 g, 0.26M). Then, hydrazine (16.5 g, 0.52M) in methanol (20 ml) was added in one portion. The reaction mixture was heated slowly to 70° C., 88° C. and 135° C. over a 5 hour period of time to remove methanol solvent and ethanol which is a condensation product of ethyl acrylate and hydrazine. After cooling a colorless liquid was obtained. The product contained 11.0 meq/g total amine. The H-nmr indicated the structure containing

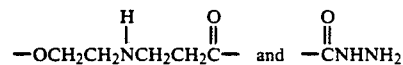

functionality.

Usage EXAMPLE II (As Epoxy Curing Agents)

The product of Example I, second step (5.0 g) and EPON ® 828 (Shell product, 15.3 g) were mixed, poured into a mold and cured at 80° C. overnight. The final material was a very hard, nearly colorless polymer.

TABLE

HYDRAZINE-TERMINATED JEFFAMINE ® AMINES

| Example | Amine* | Molar Ratio Amine:Acrylate: Hydrazine | Amine Content (calc) meq/g | Appearance |
|---|---|---|---|---|
| V | BAEE | 1:2.4:2 | — | Semisolid |
| VI | BAEE | 1:2:2 | 11.2 (14.5) | Liquid |
| VII | EDR-148 | 1:2:2 | 11.0 (12.3) | Colorless Liquid |
| VIII | EDR-148 | 1:2:2 (low temp.) | 11.9 (12.3) | Colorless liquid |
| IX | EDR-192 | 1:2:2 | 8.7 (11.0) | Liquid |
| X | EDR-192 | 1:2:2 (low temp.) | 10.2 (11.0) | Liquid |
| XI | D-230 | 1:2:2 | 8.8 (9.9) | Yellow Liquid |
| XII | D-230 | 1:2:2 | 8.6 (9.9) | Yellow Liquid |

EDA: ethylenediamine
BAEE: bisaminoethyl ether
Acrylate: methyl or ethyl acrylate

What is claimed is:

1. A composition comprising a hydrazine terminated polyoxyalkylene amine having the formula:

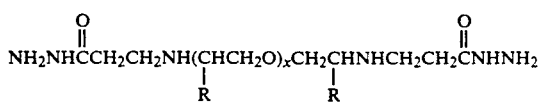

where x is a positive integer from 1 to 6 and R is hydrogen, $CH_3$ or $C_2H_5$.

2. A hydrazine terminated polyoxyalkylene amine represented by the formula:

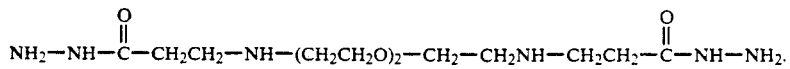
3. A hydrazine terminated polyoxyalkylene amine represented by the formula:
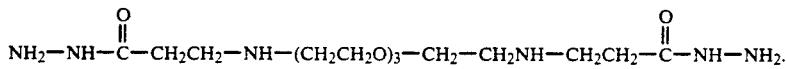
4. A hydrazine terminated polyoxyalkylene amine represented by the formula:
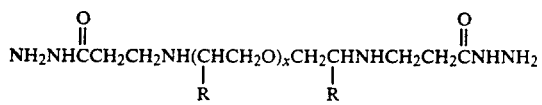
where R is hydrogen or methyl and x is 2–4.
5. A hydrazine terminated polyoxyalkylene diamine represented by the formula:
$$NH_2NHCCH_2CH_2NH(CHCH_2O)_xCH_2CHNHCH_2CH_2CNHNH_2$$
where R is hydrogen or methyl and x is 5–6.
* * * * *